(12) United States Patent
Groelz et al.

(10) Patent No.: US 8,673,241 B2
(45) Date of Patent: Mar. 18, 2014

(54) METHOD AND DEVICE FOR FIXING/STABILIZING A SAMPLE

(75) Inventors: Daniel Groelz, Solingen (DE); Christian Lenz, Duesseldorf (DE); Vera Hollaender, Unna (DE); Thomas Rothmann, Langenfeld (DE)

(73) Assignee: Qiagen GmbH, Hilden (DE)

( * ) Notice: Subject to any disclaimer, the term of this patent is extended or adjusted under 35 U.S.C. 154(b) by 168 days.

(21) Appl. No.: 12/671,354

(22) PCT Filed: Aug. 1, 2008

(86) PCT No.: PCT/EP2008/060128
§ 371 (c)(1),
(2), (4) Date: Jun. 16, 2010

(87) PCT Pub. No.: WO2009/016254
PCT Pub. Date: Feb. 5, 2009

(65) Prior Publication Data
US 2010/0267081 A1    Oct. 21, 2010

(30) Foreign Application Priority Data
Aug. 2, 2007   (EP) .................................... 07113714

(51) Int. Cl.
*A61B 10/02* (2006.01)
(52) U.S. Cl.
USPC ............ 422/536; 422/547; 422/551; 422/554
(58) Field of Classification Search
USPC .................. 422/536, 547, 551, 554
See application file for complete search history.

(56) References Cited

U.S. PATENT DOCUMENTS

| | | | |
|---|---|---|---|
| 7,147,826 B2 | 12/2006 | Haywood et al. | |
| 2003/0087423 A1 | 5/2003 | Haywood et al. | |
| 2004/0053402 A1* | 3/2004 | Stark et al. ................. | 435/287.2 |
| 2005/0147538 A1 | 7/2005 | Williamson et al. | |
| 2006/0178598 A1 | 8/2006 | Cho et al. | |
| 2007/0140920 A1 | 6/2007 | McCormick | |

FOREIGN PATENT DOCUMENTS

| | | |
|---|---|---|
| DE | 4019182 | 1/1991 |
| DE | 19820466 | 11/1999 |
| EP | 1262758 | 12/2002 |
| EP | 1 595 502 A2 | 11/2005 |
| EP | 1804045 | 7/2007 |
| WO | 03/040697 | 5/2003 |
| WO | 2005/037182 | 4/2005 |
| WO | 2006/078922 A2 | 7/2006 |

OTHER PUBLICATIONS

International Search Report of PCT/EP2008/060128, mailed Nov. 5, 2008.
Internationa Preliminary Report on Patentability based on PCT/EP2008/060128 dated Mar. 2, 2010.
Patent Examination Report No. 2 of Australia Patent Application No. 2008281720 issued Jun. 6, 2013.

* cited by examiner

*Primary Examiner* — Monique Cole
(74) *Attorney, Agent, or Firm* — Miles & Stockbridge P.C.

(57) ABSTRACT

The present invention provides a method for fixing and/or stabilizing a sample, in which the sample is put into a permeable container with a maximum overall height of 10 mm, preferably of 5 mm, and the container filled with the sample is immersed in fixing and/or stabilizing agents and the sample is fixed and/or stabilized.

18 Claims, 6 Drawing Sheets

METHOD AND DEVICE FOR FIXING/STABILIZING A SAMPLE

CROSS REFERENCE TO RELATED APPLICATIONS

This application is a §371 National Stage Application of PCT/EP2008/060128 filed Aug. 1, 2008, which claims priority to European Application 07113714.5 filed Aug. 2, 2007.

BACKGROUND OF THE INVENTION

1. Field of the Invention

The invention relates to a method and a device for the fixing and/or stabilization of a sample. Biomolecules are stabilized and/or tissues are fixed, and thus made durable. Biomolecules to be stabilized are in particular DNA, RNA and proteins.

2. Description of Related Art

Documents WO 03/040697 and DE 40 19 182 A1 disclose fixing tissue samples, dehydrating a fixed sample and embedding it in paraffin. The sample embedded in paraffin is cut into thin slices and studied under a microscope. According to document DE 40 19 182 A1, the impregnation of samples is supported with the aid of ultrasound. Document DE 198 20 466 A1 discloses disrupting a biological sample with the aid of ultrasound.

In order to be able to stabilize a biological sample, it is especially important for a stabilizing solution or stabilizing fluid to penetrate the sample, which contains the biomolecules, sufficiently quickly. In particular, when the biological sample is a tissue, it is advantageous for the tissue to be penetrated sufficiently quickly by a fixing solution or fixing fluid, for the tissue to be fixed successfully.

In the prior art, a manufacturer of a stabilizing solution specifies the boundary conditions that are to be observed during stabilization. Thus, a manufacturer of a stabilizing solution states, for example, what dimensions a sample must not exceed, for particular biomolecules, for example RNA, to be stabilized uniformly at every point of the sample. Such a statement may, for example, specify a certain thickness that a sample must not exceed, to achieve the desired stabilization. In some cases, other geometric specifications are also added. For example, a laboratory assistant must then, for example using a scalpel, adjust a sample to the desired size, before putting the sample in a stabilizing solution. Additionally, in many cases manufacturers state what ratio must be maintained between stabilizing solution and sample, in order to achieve a desired stabilization.

If tissues are to be fixed, often the manufacturer does not specify any boundary conditions that are to be observed for fixing, especially when the tissues are to be fixed for histological investigations. For histological investigations, as a rule formalin is used as fixing solution. The desired tissue is then placed in formalin and thus fixed.

Even if as a rule no requirements are stated for fixing with fixing solutions containing formaldehyde, for example formalin, nevertheless excessive size of a sample proves to be disadvantageous in the case of stabilization of tissue. Therefore even with formaldehyde-containing fixing solutions it is advisable not to exceed certain sizes or dimensions, in order to fix a tissue successfully.

Document U.S. Pat. No. 7,147,826 B2 discloses the provision of a closable, permeable basket, which is to be placed in another vessel containing a stabilizing solution. Liquid can penetrate into the permeable basket from all directions. If the basket contains a biological sample that is to be stabilized, it is necessary to ensure that the stabilizing solution can reach the sample from all directions.

Document U.S. Pat. No. 2003/0087423 A1 also discloses the provision of a permeable basket for a biological sample. However, in this case the basket is fastened to a lid of the vessel, to facilitate handling. Once again, it should be possible for a solution to reach a sample contained in the basket reliably and completely from all directions.

Document EP 1 262 758 A1 discloses a further permeable container for the preparation of tissue.

Cassettes made of plastic, with a hinged lid, are known from the prior art under the tradename "Histosette", which are intended for holding tissue samples for processing or dehydration of the tissue. The area of the bottom or lid of a Histosette is at least 3 cm*2.5 cm. Said cassette is at least 0.5 cm high or thick. Bottom and lid are in the form of a sieve or are provided with a large number of slits, so that liquid can get into the cassette, for example during dehydration of a tissue.

If Histosettes are used for dehydration of tissue, for example so that histological investigations can then be carried out, tissue that has already been fixed, for example by placing in formalin beforehand, is first cut to the desired size to fit the Histosette. Then the tissue is put in the Histosette and the Histosette is closed. The Histosette together with the tissue it contains is then put in an automatic device, in which dehydration is carried out automatically.

The dehydration steps specified in said automatic device may include a repeat treatment of the already fixed tissue with a fixing solution. However, this does not mean that the tissue is fixed in the sense of the present invention, as the tissue had already been fixed previously. Then the Histosette, with the tissue it contains, is immersed successively in various alcohol baths with higher and higher alcohol concentration. The alcohol extracts the water from the tissue. To ensure gentle dehydration of the tissue, the alcohol concentration is increased very slowly from one bath to the next.

Then the Histosette, with the tissue inside, is immersed in an intermediate medium, for example xylene. The intermediate medium displaces the alcohol present in the tissue. In contrast to alcohol, the intermediate medium is miscible with paraffin, ready for the subsequent paraffin treatment.

Next, the Histosette, with the tissue inside, is immersed in hot and hence liquid paraffin. Paraffin then penetrates into the tissue. If the paraffin has penetrated into the tissue in the desired manner, the Histosette is taken out of the automatic device. The paraffin that has already hardened somewhat, with the piece of tissue inside, is then transferred to a small container or "mold" that is open at the top, and is covered with hot, liquid paraffin, so that after the paraffin has cooled, we get a paraffin block containing the tissue. When this paraffin has cooled, we have a dehydrated sample embedded in paraffin. For carrying out histological investigations, tissue sections of micrometer thickness are prepared. These tissue sections can be mounted on slides, deparaffined, stained and assessed under the microscope. One disadvantage of fixing with formaldehyde-containing fixing solutions is that biomolecules are sometimes crosslinked irreversibly and thus destroyed. As a result, the isolation of biomolecules for analytical investigations is made difficult or impossible.

A permeable cassette with a liftable lid for the accommodation of tissue samples is known from document U.S. Pat No. 2007/0140920 A1. A sample is placed into the cassette and the cassette is closed. The sample is dewatered, cleaned and infiltrated with wax in the cassette. Fixing or stabilizing the sample before the dewatering while it is present in the cassette cannot be inferred from U.S. Pat. No. 2007/0140920 A1.

Permeable cassettes for the accommodation of biological samples are also disclosed by documents U.S. Pat. No. 2005/0147538 A1 and WO 2005/037182 A2. Both documents disclose that a sample should first be fixed. Only after the fixing is sample material placed into a cassette and treated further in the desired manner.

Document U.S. Pat. No. 2006/0178598 A1 discloses a tool with protruding, needle-shaped parts provided with hooks. The protruding, needle-shaped parts should be inserted into a sample in order then to tear sample material captured by the protruding, needle-shaped parts from the rest of the sample. The tool does not comprise any walls in the form of a sieve, slit or grating.

SUMMARY OF THE INVENTION

The aim of the invention is to provide better stabilization or fixing of biomolecules and tissues and, in one embodiment, to simplify investigation.

The aim of the invention is achieved with a method with the features stated in claim 1. An object for carrying out the method comprises the features of the secondary claim. Advantageous embodiments can be seen from the subclaims.

DETAILED DESCRIPTION OF A PREFERRED EMBODIMENT

A sample is put in a permeable container with a maximum overall height of 10 mm, preferably of 5 mm. This is achieved by virtue of the sample firstly having suitable dimensions, for example with the aid of a scalpel. The container filled with the sample is immersed in agents for fixing and/or stabilization. As a result, the sample is fixed and/or stabilized.

One of the most urgent problems in the fixing of tissue samples consists in the lack of standardization. There are no generally accepted and implemented methods as to what volume of fixing agent, for example formalin, must be used per unit volume of tissue, even though it is known that too little fixing agent can cause damage to the tissue structures in the interior of the sample as a result of autolysis. Moreover, the expression pattern of the cells in unfixed regions can shift as a result of gene induction or degradation of mRNA.

A container in the sense of the main claim has a maximum overall height of 10 mm or 5 mm, when two inside walls or correspondingly the bottom and lid of the container are not more than 10 mm or 5 mm apart. When the sample is in this container, this ensures that liquid fixing agent and/or stabilizing agent is quickly able to penetrate the sample in the container, and particularly well when the overall height is not more than 5 mm. As flow through the container is possible, liquid fixing agent and/or stabilizing agent, which can be in the form of one or more solutions, can reach the interior of the container and penetrate into the sample. The sample contained in the permeable container is only fixed or stabilized on immersion or as a consequence thereof. This means that the sample had not been fixed or stabilized previously.

Preferably the two walls or the bottom and lid of the permeable container are in the form of a sieve or are provided with slits or the like, which are not more than 10 mm, preferably not more than 5 mm apart. This arrangement is even better for ensuring that the sample in the permeable container is properly fixed and/or stabilized.

In an advantageous embodiment of the invention, the fixing and/or stabilization of the sample present in the permeable container is effected in a vessel with exactly defined dimensions, filled with an exactly defined volume of fixing and/or stabilizing solution. The size of the permeable container defines the maximum size of the tissue sample and the vessel defines the volume of fixing and/or stabilizing reagent. This has the considerable advantage that the arrangement selected achieves an exactly defined ratio of fixing and/or stabilizing reagent to tissue sample. A permeable container of exactly defined size in combination with a vessel of exactly defined size leads to a standardization of the tissue fixing. An optimally selected ratio of fixing and/or stabilizing reagent to tissue sample prevents underfixing and ensures standardization of the fixing and hence also better comparability between different samples. To implement this embodiment of the invention, a set is thus provided or specified, which comprises at least one vessel with specified dimensions in addition to the permeable container. The set preferably additionally comprises a specified fixing solution in order thus to be able to fix or stabilize a sample in a standardized manner.

The vessel with the permeable container may, in addition to the fixing, also serve as a storage vessel or for transport of the sample. In a further embodiment, the permeable container is a constituent of the vessel. For example, the permeable container may be connected by a connecting element to the lid of the accommodating vessel in which the fixing and/or stabilizing solution is present. In this way, the permeable container forms an integral constituent of the vessel. By virtue of the permeable container being connected to the lid, the container can be removed easily from the vessel for charging and discharging. It is unnecessary to grip the permeable container with aids such as tweezers or the like. The risk of contamination or contact with potentially toxic fixing reagents is minimized in this way. If the tissue sample has to be passed through several solutions, this can be performed in a simplified manner. All solutions required are filled into vessels of the same design and same dimensions. A lid which fits these vessels contains, via a connecting element, the permeable container. After charging with the tissue sample, the lid is placed successively onto the different vessels without any need to remove the sample from the permeable container for the transfer.

In a further embodiment, the permeable container is not an integral constituent, for example the lid of the vessel, but may be secured to the lid by a fastener. This fastener may be secured directly below the lid or on a connecting element which is connected to the lid. The advantage of this arrangement is that the permeable container can be charged dry, since it has not come into contact with potentially toxic fixing reagents in the vessel before it is charged with the tissue sample.

In a further configuration, the permeable container which is connected to the lid of a vessel via a connecting element can be removed from the lid by a simple mechanical manipulation. For example, the connecting element may contain a predetermined breaking point close to the permeable container. In a further configuration, the permeable container can be removed by means of an ejection device present on the lid of the accommodation vessel. For example, the permeable container, in one embodiment, can be ejected by mechanical pressure, the pressure being exerted by a plunger present within the connecting element. The plunger rests on the permeable container at one end and projects out of the lid of the vessel at the other end. External pressure on the plunger ejects the permeable container. The advantage of such a device would be that the permeable container need not be handled or manipulated for transfer into, for example, an automatic dehydrator or another solution.

In one embodiment of the invention, the dimensions of the permeable container are selected such that the permeable container can be used in an automatic dehydrator, so that the sample in the permeable container can be dehydrated following fixing or stabilization. It is not then necessary to transfer the sample from one permeable container to another container, if the sample is to be dehydrated following fixing or stabilization. One process step is thus avoided. It is, however, also possible to carry out fixing and/or stabilization in the automatic dehydrator. Before it has been fixed or stabilized, the sample is first immersed by the automatic dehydrator in a fixing solution and/or stabilizing solution or comparable agents. This is mainly economically worthwhile when the sample is sufficiently thin and therefore fixing or stabilization can be achieved relatively quickly.

Formalin can be used as fixing agent, if only histological investigations are to be carried out. If, however, biomolecules are to be stabilized for subsequent investigations, and thus made durable, it is necessary to select a suitable stabilizing solution or stabilizing agent, as this is not possible with formalin. For stabilizing the RNA of a sample, RNAlater® from the U.S. Pat. No. company Ambion can be used as stabilizing solution. Another example for the simultaneous stabilization of DNA, RNA and proteins is the stabilizing solution Allprotect™ Tissue Reagent from the German company Qiagen GmbH. One example of the stabilization of the morphology for histological studies as well as the DNA, RNA and protein biomolecules in tissue samples is the commercially available PAXgene® Tissue stabilizing and fixing agents. All of the examples cited are thus stabilizing and fixing agents in the sense of the present teaching.

Preferably, a polyol-containing composition is used as agent for fixing and stabilizing a sample. With such a composition, fixing and stabilizing can be carried out particularly well and simply, as can be seen from document EP 1 804 045 A1. The disclosures in these documents, from which further advantageous embodiments of such an agent can be seen, are incorporated hereby as an advantageous embodiment of the claimed method.

For simultaneous stabilization and fixing of a biological sample, the sample is contacted in particular in the claimed manner with a composition comprising 1 to 100 wt. % of at least one polyol and 0 to 99 wt. % of at least one additive, the total amount of the two stated components being 100 wt. %.

The polyol is in particular a diol, triol, tetraol, pentaol, hexaol, heptaol, octaol or nonaol, diol or triol being especially preferred. Preferably the polyol has 2 to 20 carbon atoms.

In an advantageous embodiment the polyol is selected from the group comprising 1,2-ethanediol, 1,2-propanediol, 1,3-propanediol, 1,2-butane-diol, 1,3-butanediol, 1,4-butanediol, 2,3-butanediol, 1,2-pentanediol, 1,3-pentanediol, 1,4-pentanediol, 1,5-pentanediol, 2,3-pentanediol, 2,4-pentanediol, 1,2-hexanediol, 1,3-hexanediol, 1,4-hexanediol, 1,5-hexanediol, 1,6-hexanediol, 2,3-hexanediol, 2,4-hexanediol, 2,5-hexanediol, 3,4-hexanediol, 1,2,3-propanetriol, 1,2,3-butanetriol, 1,2,4-butanetriol, 1,2,3-pentanetriol, 1,2,4-pentanetriol, 1,2,5-pentanetriol, 2,3,4-pentanetriol, 1,2,3-hexanetriol, 1,2,4-hexanetriol, 1,2,5-hexanetriol, 1,2,6-hexanetriol, 2,3,4-hexanetriol, 2,3,5-hexanetriol, 3-methyl-1,3,5-pentanetriol, trimethylolpropanol, pentaerythritol, diethylene glycol, dipropylene glycol, triethylene glycol, tripropylene glycol, polyethylene glycol and polypropylene glycol.

Especially preferably, the composition comprises a mixture of at least two polyols.

The additive is preferably selected from the group comprising detergents, inhibitors, which inhibit the degradation of nucleic acids or proteins, viscosity regulators, dyes, buffer compounds, preservatives, complexing agents, reducing agents, substances that improve the permeability of cells, chaotropic substances, fixatives, solvents other than polyols and mixtures of at least two of these additives.

In a preferred embodiment the method comprises a histological analysis of the biological sample contacted with the composition and/or analysis of biomolecules in the or from the biological sample contacted with the composition.

According to the prior art, a sample is fixed completely or partially for example using formalin, when the sample is to be investigated histologically. An unfixed portion of this sample is treated with a stabilizing agent, if supplementary stabilization of biomolecules is required. In contrast, the method according to the invention provides a simplification of subsequent operations mainly when the sample inside the container is treated with a fixing and stabilizing agent, for example that described in PCT/EP/2008052371, which simultaneously fixes the tissue of a sample and stabilizes biomolecules of said sample. Therefore in a preferred embodiment the solution or liquid is selected so that biomolecules and tissue can be made durable simultaneously.

According to document PCT/EP/2008052371, the morphology and biomolecules in a biological material are fixed and stabilized, the method comprising the following steps:
 i) providing a biological material, and
 ii) contacting the biological material with a first nonaqueous composition comprising:
  (a1) 10 to 90 vol. % methanol and
  (a2) at least one additional additive and
  (a3) optionally an acid,
 iii) transferring the biological material into a second composition
  (B), comprising up to 99 vol. % ethanol.

As a first composition in step ii), a nonaqueous composition (A) for preserving biological material is particularly useful, which nonaqueous composition (A) comprises the following:
 (α1) 10 to less than 80 vol. % methanol and
 (α2) at least one additional additive and
 (α3) an acid.

Component (α1) of composition (A) is methanol. Methanol is present in composition (A) to an extent of 10 to less than 80%; methanol is preferably present to an extent of about 70 vol. %, to an extent of about 60 vol. % or to an extent of about 50 vol. %.

The at least one additive (α2) of compositions (A) or (a2) of the first composition of step (ii) of the above-described method may be an additional solvent other than methanol, or an additive which is selected from the group comprising detergents and inhibitors which inhibit the degradation of nucleic acids or proteins, DEPC, alkylating agents, acetylating agents, halogenating agents, nucleotides, nucleotide analogs, amino acids, amino acid analogs, viscosity regulators, dyes, buffer substances, preservatives, complexing agents, reducing agents, oxidizing agents, substances which improve the permeability of cells, chaotropic substances, for example guanidinium isothiocyanate or guanidinium hydrochloride, or chaotropic salts with anions, and mixtures of at least two to six of these additives.

Preferred additional additives are C2- to C12-polyols, polyethylene glycol (PEG) and diethylene glycol monoethyl ether acetate (DEGMEA) and chloroform. According to the present invention, it is preferred that the additional component of composition A is not chloroform. The PEG preferably has a melting point below ambient temperature.

The solvent other than methanol may be an organic solvent which is preferably selected from the group comprising monohydric alcohols (monools), C2-C12-polyols, ketones, dimethyl sulfoxide, aromatic hydrocarbons, halogenated hydrocarbons, ethers, carboxylic acids, carboxamides, nitriles, nitroalkanes and esters, suitable solvents being selectable, for example, from the group of ethanol, 1-propanol, 2-propanol, 1,3-butanediol, 1,4-butanediol, acetonitrile, acetone, anisole, benzonitrile, 1-methoxy-2-propanol, quinoline, cyclohexanone, diacetin, dichloromethane, chloroform, xylene, diethyl ether, dimethyl ether, toluene, dimethyl ketone, diethyl ketone, dimethyl adipate, dimethyl carbonate, dimethyl sulfite, dioxane, dimethyl sulfoxide, methyl acetate, ethyl acetate, benzoic acid, methyl benzoate, ethyl benzoate, ethylbenzene, formamide, glyceryl triacetate, ethyl acetoacetate, methyl acetoacetate, N,N-diethylacetamide, N-methyl-N-ethylacetamide, N,N-dimethylacetamide, N,N-dimethylformamide, N-methyl-N-ethylformamide, N,N-diethylformamide, N,N-dimethylthioformamide, N,N-diethylthioformamide, N-methyl-N-ethyl-thioformamide, N,N-dimethylacetamide, N-methyl-N-ethylacetamide, N,N-diethylacetamide, nitroethane, nitromethyltoluene and triethyl phosphate. Preferably, the composition A and/or the nonaqueous composition in step ii) comprises no halogenated carbohydrate, especially no chlorinated carbohydrate, especially chloroform and/or trichloroethane.

The concentration of components ($\alpha 2$) and (a2) may, according to document PCT/EP/2008052371, be about 50% to 1% (vol./vol.), preferably about 20%.

Component ($\alpha 3$) of composition (A) or the optional component (a3) of the first composition which is used in step (ii) of the process described in document PCT/EP/2008052371 is an organic or inorganic acid, preferably a weak acid, most preferably acetic acid or propionic acid.

Composition (A) can be used as the first composition in step ii) of the method according to the present invention. However, it is emphasized explicitly that composition (A) can also be used in a method for treatment or preservation of biological material without the "transfer step" iii). In addition, the first composition in step ii) of the method according to the present invention may be a composition other than composition (A), provided that the first composition in step ii) as defined above comprises methanol as the main ingredient.

According to document PCT/EP/2008052371, the method for treatment of the biological material includes a "transfer step" iii), in which the biological material is transferred into a second composition (B) which comprises up to 99 vol. % ethanol. The transfer step is especially suitable for storing the biological material.

The particular advantages of the method claimed become particularly clear when the method described in document PCT/EP/2008052371 is employed. In one embodiment, the sample present in the permeable container is fixed with the composition A in a vessel and then transferred into a vessel containing composition B. For this transfer of composition A to composition B, the sample need not be transferred from a permeable container into a further container.

In a further configuration, the permeable container is connected by a connecting element to the lid of the accommodation vessel in which the composition A is present. When both vessels containing compositions A and B possess the same dimensions, the sample present in the permeable container can be transferred with the aid of the lid, in which case the lid seals the vessel containing composition B tight. This does not necessitate touching or opening the permeable container. In this embodiment, the vessel containing composition B can simultaneously be used as a storage vessel or else for transport of the sample into, for example, a pathology laboratory.

Advantages and further details of the different embodiments are evident from the international patent application with reference number PCT/EP/2008052371.

In a further embodiment, the method comprises a histological analysis of the biological sample contacted with the composition and/or analysis of biomolecules in the or from the biological sample contacted with the composition. Preferably both the analysis of tissue histology and the analysis of biomolecules are included.

Preferably both the analysis of proteins and the analysis of nucleic acids are included.

In one embodiment the sample contains organisms, isolated cells, organelles, bacteria, fungi or parts of fungi, viruses, viroids, prions, tissues, tissue fragments, tissue sections, body fluids, natural, optionally isolated proteins, synthetic or modified proteins, natural, optionally isolated nucleic acids, synthetic or modified nucleic acids, other biomolecules, for example lipids, carbohydrates, metabolic products and metabolites, plants or parts of plants, feces, smears, aspirates, food samples, environmental samples and/or forensic samples.

Advantages and further details of various other embodiments are given in EP 1 804 045 A1 or in the international patent application with reference number PCT/EP/2008052371.

An agent that, for a sample, both fixes the morphology of the tissue and stabilizes biomolecules, is chosen in particular when the histology of the tissue is investigated first and then, depending on the histological findings, biomolecules are optionally also to be isolated and analyzed.

In one embodiment the permeable container is connected completely or partially following removal of water with a paraffin block, into which the sample, first fixed and/or stabilized and then dehydrated, had been brought in a manner known from the prior art. Connection can be achieved by mounting the permeable container completely or partially on a "mold" with a permeable wall, in which the sample, already provided with paraffin, is immersed in paraffin. Further paraffin is added from above, through the permeable wall. Paraffin additionally passes through the permeable wall from the container or portion of the container into the "mold" and encloses the permeable wall. After the paraffin has cooled, the container or a portion of the container is joined to this paraffin block.

The container or the portion thereof joined to the paraffin block now forms a handle or holder, with which the paraffin block, with the sample inside, can be extracted from the "mold". This holder can now be used for clamping the paraffin block, with the sample inside, in an automatic device or semiautomatic device, by means of which desired tissue sections can be cut from the sample. Such an automatic or semiautomatic device is known as a microtome.

Preferably, therefore, in one embodiment the microtome and the permeable container are designed for one another, so that the container can be clamped completely or partially in the microtome in the stated manner.

If histological investigations have been carried out and biomolecules are now to be processed, routinely first the paraffin is to be removed from the part of the paraffined sample that is to be further processed. For example, for investigation of biomolecules, further sections are prepared with the microtome. These sections are collected in a microcentrifuge container and first the paraffin is removed, essentially in a procedure that is the reverse of dehydration. First an intermediate solution is added, in order to dissolve the paraffin. Then the tissue sample is centrifuged and the supernatant with the paraffin dissolved in the intermediate solution is removed. Then the tissue pellet is resuspended in pure alcohol, in order to displace the intermediate solution. After a second centrifugation and removal of the supernatant, the tissue pellet can be taken up in a suitable lysis buffer and processed according to the prior art. The purified biomolecules can then be used for the desired investigations.

In an advantageous embodiment, within the scope of a histological investigation a microscope is used that is equipped with a laser. If tissue is investigated histologically by means of the microscope and an interesting region is found, this region can be cut out very accurately with the laser. By means of the present invention, it is now particularly easy for this excised region to be investigated immediately with respect to biomolecules. If the excised region is very small, this portion of the tissue can be transferred directly to a lysis buffer, in order to isolate biomolecules such as DNA, RNA and/or protein for more detailed investigation.

In one embodiment of the invention, the permeable container, which suitably restricts the size and in particular the thickness of a tissue that is to be fixed, has on one side and preferably on a narrow side, a sharp-edged opening. The sharp-edged opening is provided for pushing into a sample that is to be fixed and/or stabilized. With a rotary movement, the portion of the sample that is then in the permeable container can be separated and removed. The permeable container is then provided laterally preferably with holes and the like, for example like a sieve. The tissue inside the permeable container then has dimensions that are especially suitable for fixing and/or stabilization.

Especially in the embodiment with the sharp-edged opening, the permeable container is secured to a lid, with which a vessel, with means therein for fixing and/or stabilization, is closed. The lid then fulfills a dual function. On the one hand it serves for closing the vessel with the agent inside for fixing and/or stabilization, during fixing or stabilization, which as a rule takes at least several hours. On the other hand the lid serves as a handle, to enable the permeable container to be pushed simply into a sample. In this way, manipulation is particularly simple.

In one embodiment of the invention, the permeable container, which preferably includes a sharp-edged opening, is provided with a plunger, which for example can be inserted from above through a lid serving as handle and into the permeable container. In this way it is particularly easy for tissue inside the permeable container to be pushed back out.

This is advantageous in particular when biomolecules are to be investigated immediately, i.e. following stabilization. The stabilized sample can then be pushed out of the permeable container with the plunger, and preferably into the appropriate solution with which the investigation of the biomolecules is started. Generally it is first a buffer solution, into which the sample from which the biomolecules are to be investigated is put.

The provision of a plunger is also advantageous because, defined in this way, only a portion of the fixed or stabilized sample can be pushed out of the permeable container. This portion of the sample then projecting from the permeable container can then be cut off, to be used for example for investigation of biomolecules. The remainder can then for example be used for histological investigations.

If biomolecules are to be investigated, basically it is necessary to disrupt and hence homogenize the sample. In the prior art this is done for example with ultrasound. However, with the prior art there is a risk that this may damage the molecules of interest. Therefore, in one embodiment of the invention, the permeable container with the stabilized sample inside is put in another vessel containing a liquid. An ultrasound source is positioned so that ultrasound impinges on the permeable container and in particular is focused on the permeable container. If the sample in the permeable container is comminuted by the ultrasound, the comminuted pieces of tissue can pass through suitably permeable walls of the permeable container and into the liquid, which for example can be the stabilizing agent. In this way comminuted fragments can escape, so that they are no longer exposed to the ultrasound, which would now be disadvantageous. This reduces the risk of the molecules of interest being damaged in an undesirable manner through overexposure during disruption of the sample.

In the aforementioned embodiment, the ultrasound source is in particular adjusted and restricted in such a way that essentially it only takes in the permeable container with the sample inside, and in this sense is focused on the permeable container.

Basically, instead of ultrasound it is possible to choose some other means by which the sample inside the permeable container is disrupted, with the result that sufficiently comminuted portions of the sample escape to the outside and so are advantageously excluded from further mechanical treatment.

The invention is explained in more detail with reference to the following drawings.

FIGS. 1A and 1B show a typical basic form of the permeable container, which is used for fixing a sample. The container comprises a front 1 of relatively large area and a back, which are for example in the form of gratings, and therefore a liquid can flow through them. The front can be a hinged lid and the back will be the bottom of the permeable container. The distance between front and back is relatively small and is only a few millimeters and in particular not more than 5 millimeters. This ensures that a sample inside the permeable container can be impregnated sufficiently quickly by a fixing solution. The walls 2 and 3 of the permeable container can also be permeable. For reasons of stability, however, solid, closed walls 2 and 3 are to be preferred.

FIG. 2 shows a side view of the permeable container with front wall 1, which is secured by a web 5 to a lid 4 and is preferably detachable, for example by positive locking, e.g. by snap-fitting connectors. On the one hand the lid can then be used as a handle, for holding the permeable container without contaminating it, or conversely without being contaminated by the container or its contents. On the other hand the lid can serve for closing a vessel containing the means for fixing and/or stabilizing, when the permeable container is to be immersed in an appropriate fluid. If it is necessary for fixing or stabilization to transfer a sample from one solution to another, the sample inside the permeable container can be transferred by means of the lid, without having to open the permeable container. Owing to the detachable attachment, the permeable container can be used further, for example for transferring the permeable container, with the fixed or stabilized sample inside, to a correspondingly adapted automatic dehydrator.

In the embodiment shown in FIG. 1A and FIG. 2, the underside 6 of the container is preferably open or can be opened. The edges are then made sharp-edged, so that said underside can be pushed into a typical sample, in order to fill the container with sample material and at the same time give the sample material suitable dimensions.

FIG. 3 shows an embodiment with a plunger 7, with which sample material can be pushed out of the permeable container. The plunger 7 is inserted into the top side of the container which is open.

On cost grounds, the permeable container is preferably made of plastic. It is then in particular a disposable article. A brand-new permeable container is then used for each new sample, which simplifies handling.

A permeable container can, however, also be made of metal, mainly when it is to have a sharp edge for pressing into tissue.

FIG. 4 shows the construction of a permeable container with a stabilized sample inside, which is immersed in a vessel containing a liquid 8. The permeable container is located near a vessel wall 9 and is preferably secured to the lid of the vessel, and is in particular detachable and/or is positive-locking. An ultrasound source 11 is positioned close to this vessel wall 9 and is dimensioned so that ultrasound reaches the permeable container but does not go farther into the vessel, as is indicated by the arrows. Ultrasound thus disrupts the sample contained in the permeable container, which can then escape through a grating-type wall into the liquid 8, which is on the outside of the permeable container. So that ultrasound can get into the permeable container, the ultrasound is aligned so that it impinges on a permeable wall.

Figure 1A:
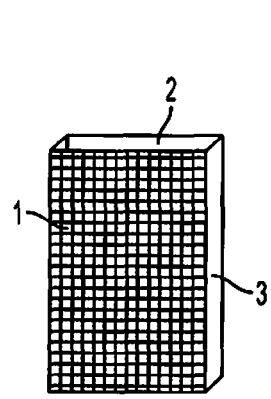
Figure 1B:
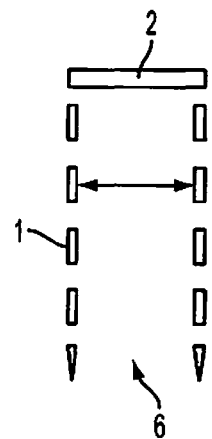
Figure 2:
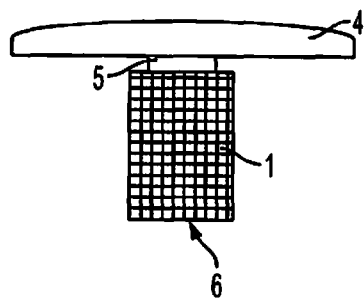
Figure 3:
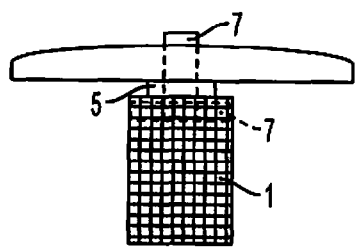
Figure 4:
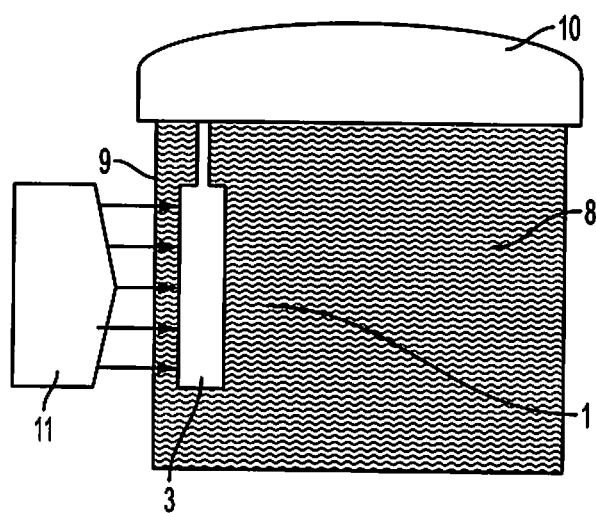

The invention is now described in more detail with reference to examples which follow. The examples are provided merely for the purpose of illustration and must not be interpreted such that they restrict the invention to the embodiments disclosed.

EXAMPLE 1

RNA Stabilization in Tissue which has been Fixed in a Permeable Container

Rat liver, kidney and spleen, directly after removal, were cut into slices with a thickness of about 3 mm. For fixing, the tissue samples were arranged in a permeable container with a length of 4 cm, a width of 2.7 cm and a depth of 5 mm. The permeable container containing the tissue samples was immersed completely into a 500 ml bottle filled with 250 ml of a fixing solution according to composition A of PCT/EP/2008052371. The fixing solution comprised methanol, acetic acid, 1,3-butanediol and PEG300. After 2 hours, the fixing was ended by transferring the tissue samples in the permeable container into another 500 ml bottle which was filled with 250 ml of a solution according to composition B of PCT/EP/2008052371, comprising ethanol (p.a.) and 1,3-butanediol.

After incubating for 20 h, the samples in the permeable container were transferred into 70% ethanol as the first processing step.

The tissue processing, which comprised dehydration, clarification and infiltration with paraffin, was performed in automated manner using a Leica TP1020 processor. The permeable container was conducted through ethanol with increasing concentrations. As an intermediate step between dehydration and infiltration with the embedding medium, clarification was carried out with xylene. Cavities and cells in the tissue were impregnated with liquid paraffin (Paraplast XTRA with low melting point, Roth Inc.) at 56° C. (details in Table 1). In order to obtain the carrier needed for microtomy, the samples were embedded into the same paraffin as was used for infiltration.

The starting material used for the RNA extraction was fresh slices from the paraffin blocks. The paraffin blocks were cut with a rotary microtome (Leica RM2245), cutting 5 slices with a thickness of 10 µm each from each sample and collecting them in a microcentrifuge tube. The removal of the paraffin was carried out by adding 1 ml of xylene, vortexing and centrifuging at 14000 rpm for 2 min. The supernatant was removed and the pellet was dissolved in 1 ml of 100% ethanol.

After centrifuging at 14000 rpm for 2 min and removing the ethanol, the pellet was dissolved in 150 µl of the RLT buffer (commercially available from QIAGEN GmbH, Germany) (containing GTC, pH=7, comprising 0.143 M β-mercaptoethanol). After adding 295 µl of water and 5 µl of proteinase K (>600 mAU/ml), the digestion was carried out at 55° C. on a shaker/incubator at 1400 rpm with a duration of 10 min. For homogenization, the lysate was supplied to a QIA shredder spin column (commercially available from QIAGEN GmbH, Germany) and centrifuged at 14000 rpm for 2 min. The permeated material was mixed with 1225 µl of ethanol (100%) and fed to an RNeasy MinElute spin column (commercially available from QIAGEN GmbH, Germany). The lysates were conducted through the membrane by the centrifugation, such that the RNA was absorbed by the membrane. Contaminants were removed by washing the membrane twice with RW1 wash buffer (commercially available from QIAGEN GmbH, Germany), comprising GTC, at pH=7.5 and ethanol. Between the two washing operations, remaining DNA was removed from the membrane by pipetting 10 µl of DNase (about 30 Kunitz units), mixed with 70 µl of RDD buffer (commercially available from QIAGEN GmbH, Germany) at pH 7.5, onto the membrane and incubating at ambient temperature for 15 min. After two further washing operations with 500 µl of the RPE buffer (commercially available from QIAGEN GmbH, Germany) (with pH=7.5 and 80% ethanol), the membrane was dried by centrifuging at maximum speed, 14000 rpm, for 1 min. Finally, the RNA was eluted by pipetting 30 µl of BR5 buffer (commercially available from QIAGEN GmbH, Germany) (pH=7) onto the membrane, followed by incubating at ambient temperature for 1 min and centrifuging at 14000 rpm for 1 min. All extractions were performed in triplicate.

The intactness and size distribution of the overall RNA was analyzed on an Agilent 2100 Bioanalyzer using the RNA 6000 Nanoassay according to the manufacturer's instructions.

Figure 5:
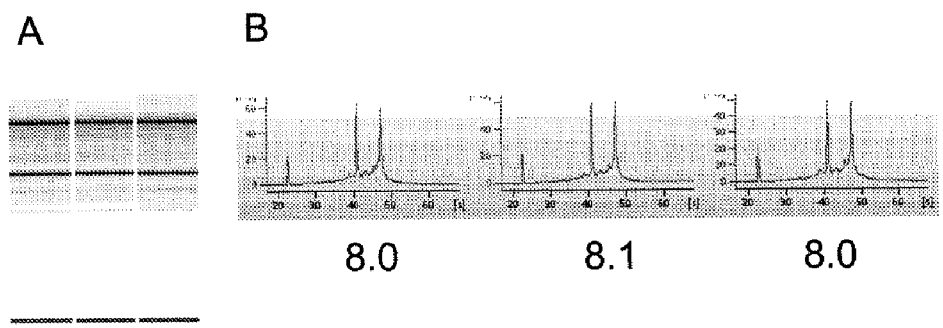
FIG. 5 shows the analysis, explained in Example 1, of RNA preparations from rat liver on an Agilent Bioanalyzer, A: Agilent gel, B: electropherogram and RIN value.
Figure 6:
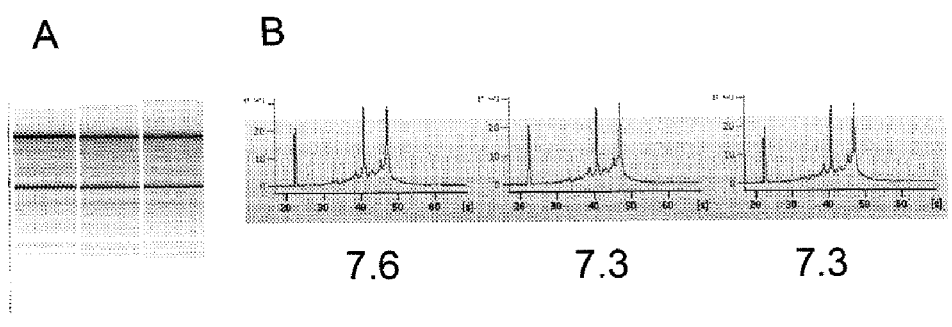
FIG. 6 shows the analysis, explained in Example 1, of RNA preparations from rat kidney on an Agilent Bioanalyzer, A: Agilent gel, B: electropherogram and RIN value.
Figure 7:
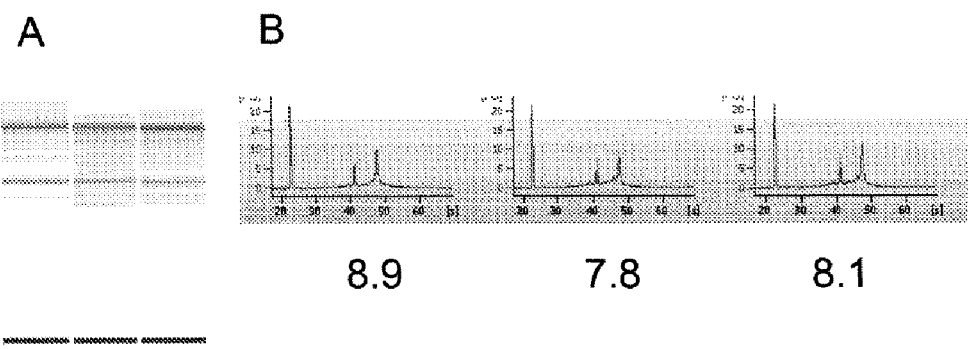
FIG. 7 shows the analysis, explained in Example 1, of RNA preparations from rat spleen on an Agilent Bioanalyzer, A: Agilent gel, B: electropherogram and RIN value.

FIGS. 5 to 7 show the Agilent gels, the corresponding electropherograms and RIN values ("RNA integrity numbers") for triplicate analyses of liver, kidney and spleen.

The analysis of the RNA on the Agilent Bioanalyzer showed all main features of an RNA with high molecular weight without degradation. On the gel (FIGS. 5-7, A), two ribosomal bands of 18S- and 28S-rRNA are visible as sharp bands virtually without distortion. On the electropherogram (FIGS. 5-7, B), the two bands correspond to two ribosomal maxima. The RIN values of the RNA vary between 7 and 9 on a scale from 1 to 10.

Conclusion: The fixing in a permeable container in combination with the fixing chemistry described in PCT/EP/2008052371 results in preservation of RNA in tissue samples, even after processing and paraffin embedding.

TABLE 1

Processing of tissue samples in the permeable container on a Leica TP1020 tissue processor

| Step | Medium | Time | Temperature |
|------|--------|------|-------------|
| 1 | 70% ethanol | 15 min | |
| 2 | 80% ethanol | 30 min | |
| 3 | 90% ethanol | 60 min | |
| 4 | 99% ethanol | 60 min | |
| 5 | 99% ethanol | 60 min | |
| 6 | Isopropanol | 60 min | |
| 7 | Isopropanol | 60 min | |
| 8 | Xylene | 60 min | |
| 9 | Xylene | 60 min | |
| 10 | Paraplast-XTRA and xylene (1:1 mixture) | 60 min | 50° C. |
| 11 | Paraplast-XTRA | 60 min | 56° C. |
| 12 | Paraplast-XTRA | 90 min | 56° C. |

EXAMPLE 2

DNA Stabilization in Tissue which has been Fixed in a Permeable Container

Tissue samples of rat liver, kidney, spleen and intestine were, as described in Example 1, stabilized in reagents of compositions A and B according to PCT/EP/2008052371 in the permeable container, processed and embedded in paraffin (with slight alterations: fixing in 300 ml of reagent of composition A and ending of the fixing after 6 h).

The starting material used for the DNA extraction was fresh slices from the paraffin blocks. The paraffin blocks were cut with a rotary microtome (Leica RM2245), cutting 5 slices with a thickness of 10 µm each from each sample and collecting them in a microcentrifuge tube. The removal of the paraffin was carried out by adding 1 ml of xylene, vortexing and centrifuging at 14000 rpm for 2 min. The supernatant was removed and the pellet was dissolved in 1 ml of 100% ethanol. After centrifuging at 14000 rpm for 2 min and removing the ethanol, the pellet was incubated at 37° C. for 10 min in order to evaporate off residual ethanol.

The pellet thus obtained was dissolved in 180 µl of ATL buffer (commercially available from QIAGEN GmbH, Germany) (pH 8.3-8.5) and digested by adding 20 µl of Proteinase K (activity 600 mAU/ml). Proteinase digestion proceeded at 56° C. for one hour with constant, gentle mixing of the samples (1400 rpm). The RNA was removed from the samples by adding 4 µl of RNase A (100 mg/ml) and incubating at ambient temperature for 2 min. After adding 200 µl of AL lysis buffer (commercially available from QIAGEN GmbH, Germany) (comprising GuHCl, pH 6.0), incubating at 70° C. for a further 10 min and adding 200 µl of ethanol (100%), the lysates were pipetted onto the silica membrane of a DNeasy® mini-spin column (commercially available from QIAGEN GmbH, Germany). The lysates were conducted through the membrane by centrifuging (1 min, 8000 rpm), such that it was possible to absorb the DNA from the membrane. Impurities were removed by washing the membrane with 500 µl of AW1 buffer (commercially available from QIAGEN GmbH, Germany) (GuHCl, containing 57% EtOH) and a second washing operation with AW2 buffer (commercially available from QIAGEN GmbH, Germany) (pH 7.5, containing 70% EtOH). The wash reagents were each conducted through the membrane by centrifuging at 8000 rpm for 1 min in each case. After the last washing operation, the membrane was dried by centrifuging at maximum speed of 14000 rpm for 3 min. Finally, the DNA was eluted by pipetting 50 µl of AE elution buffer (commercially available from QIAGEN GmbH, Germany) (10 mM Tris-Cl with pH 9.0, 0.5 mM EDTA) directly onto the membrane, followed by incubating at ambient temperature for 1 min and centrifuging at 14000 rpm for 1 min. All extractions were performed in triplicate.

The intactness and the size of the overall DNA was analyzed by agarose gel electrophoresis. This involved mixing 10 µl of the appropriate eluate with 5 µl of eluent buffer (comprising 50% glycerol and bromophenol blue). The samples were applied to 0.8% agarose gel in 1×TBE buffer. The electrophoresis was performed at about 3.3 volts per cm of length of the electrophoresis chamber over a period of 120 min. The DNA was visualized by staining with ethidium bromide.

Figure 8:
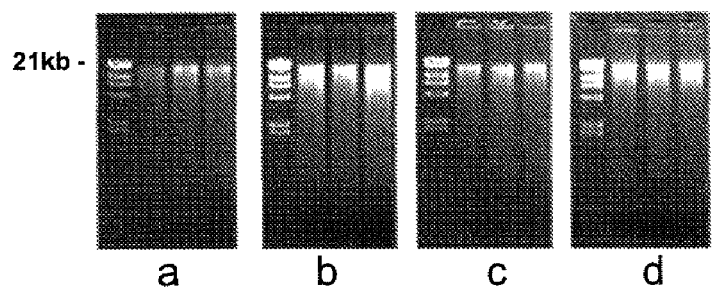
FIG. 8 shows DNA analyzed on agarose gel, which has been produced according to Example 2 from (a) rat liver, (b) rat kidney, (c) rat spleen and (d) rat intestine.

The agarose gel electrophoresis showed that the DNA had a high molecular weight. On the agarose gel (FIG. 8), the DNA from (a) liver, (b) kidney, (c) spleen and (d) intestine can be seen as clear individual bands with a molecular weight of about 21 kD. There is virtually no evident distortion indicating DNA degradation.

Conclusion: Fixing in a permeable container in combination with the fixing chemistry described in PCT/EP/2008052371 results in preservation of DNA with high molecular weight in tissue samples, even after processing and paraffin embedding.

EXAMPLE 3

Preservation of the Histology of Tissue Fixed in a Permeable Container

Tissue samples of rat liver, kidney, spleen and intestine were fixed and stabilized in reagents of compositions A and B according to PCT/EP/2008052371 in the permeable container as described in Example 1. Subsequently, the samples were processed and embedded in paraffin. In contrast to Example 1, fixing lasted 6 h and processing was commenced 30 h after transfer into a reagent with composition B according to PCT/EP/2008052371. The processing on a Leica TP1020 instrument was performed according to the protocol described in Table 1, using Neoclear instead of xylene in steps 8-10 and a temperature of 60° C. in the infiltration with paraffin (steps 11 and 12, Table 1).

For histological analysis, by means of a rotary microtome (Leica RM2245), tissue sections with thicknesses of 4 µm were prepared and secured on glass plates. Staining with hematoxylin and eosin was performed manually with dyes from Sigma Inc., observing a standard protocol (Table 2).

Figure 9:
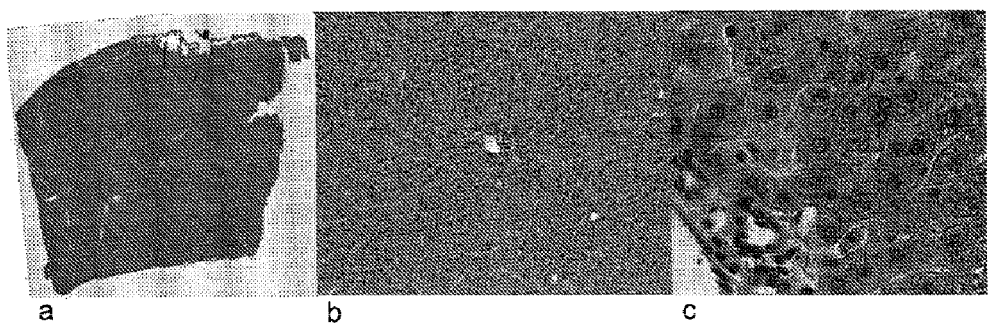
FIG. 9 shows a hematoxylin/eosin stain of rat liver (a) in overview, and (b) with 100-fold and (c) with 630-fold magnification. The tissue was fixed and processed according to Example 3.
Figure 10:
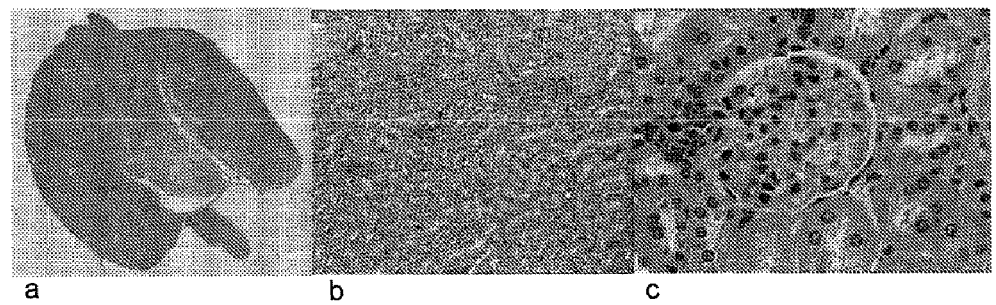
FIG. 10 shows a hematoxylin/eosin stain of rat kidney (a) in overview, and (b) with 100-fold and (c) with 630-fold magnification. The tissue was fixed and processed according to Example 3.
Figure 11:
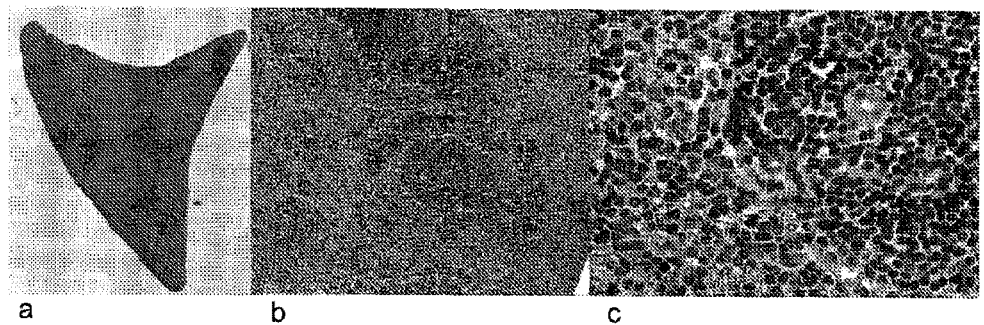
FIG. 11 shows a hematoxylin/eosin stain of rat spleen (a) in overview, and (b) with 100-fold and (c) with 630-fold magnification. The tissue was fixed and processed according to Example 3.

FIGS. 9 to 11 show the morphology of liver (FIG. 9), kidney (FIG. 10) and spleen (FIG. 11). From left to right, first an overview over the entire section, followed by 100- and 630-fold magnifications, are shown.

The overviews show that the overall morphology and the cellular structure of the individual tissues are intact. Higher magnifications (100-fold) show typical morphological structures such as liver lobules (FIG. 9), kidney glomeruli (FIG. 10) and follicles with germinal center in the spleen (FIG. 11).

At even higher magnification (630-fold), individual cells can be distinguished. The cell nucleus is visible against the cytoplasma, and various cell types can be identified.

Conclusion: Fixing in a permeable container in combination with the fixing chemistry described in PCT/EP/2008052371 results in particularly advantageous preservation of the histology in tissue samples.

TABLE 2

Staining protocol with hematoxylin and eosin

| Incubation/medium | Duration [min] |
|---|---|
| incubation at 70° C. | 10 |
| Rotihistol (xylene substitute, Roth Inc.) | 10 |
| Rotihistol | 10 |
| 96% ethanol | 5 |
| 80% ethanol | 5 |
| 70% ethanol | 5 |
| 60% ethanol | 5 |
| water | 3 |
| Mayer's hematoxylin | 5 |
| water | 0.5 |
| 70% ethanol with 1% HCl | 0.5 |
| water | 5 |
| eosin | 5 |
| water | 1 |
| 96% ethanol | 3 |
| 96% ethanol | 5 |
| 100% isopropanol | 10 |
| Rotihistol | 10 |
| Rotihistol | 10 |
| mounting with Entellan | |

The invention claimed is:

1. A permeable container for carrying out a method for fixing and/or stabilizing a sample, the container comprising a front wall, a back wall spaced apart from the front wall, and side walls coupling the front wall and the back wall,
   wherein an overall height of the container is not more than 10 mm,
   wherein the container comprises a top wall and an open bottom end opposite the top wall, and
   wherein the bottom end of the container has a sharp-edged opening.

2. The permeable container as claimed in claim 1, wherein the container further comprises a lid that connects thereto detachably.

3. The permeable container as claimed in claim 1, wherein the container further comprises a plunger inserted through the top wall for pushing a sample out of the permeable container.

4. The permeable container as claimed in claim 1, with an unfixed and unstabilized sample inside the permeable container.

5. The permeable container as claimed in claim 1, wherein the front wall and the back wall comprise gratings.

6. The permeable container as claimed in claim 1, wherein a distance between the front wall and the back wall is not more than 5 mm.

7. The permeable container as claimed in claim 1, wherein the side walls are permeable.

8. The permeable container as claimed in claim 1, wherein the side walls are solid.

9. The permeable container as claimed in claim 1, wherein the container comprises a plastic.

10. The permeable container as claimed in claim 1, wherein the container comprises a metal.

11. The permeable container as claimed in claim 1, wherein an overall height of the container is not more than 5 mm.

12. The permeable container as claimed in claim 1, wherein the container is filled with the sample and immersed in a stabilizing agent or a fixing agent.

13. The permeable container as claimed in claim 1, wherein the front wall and the back wall, which are not more than 10 mm apart, are in the form of a sieve or grating, or are provided with slits.

14. The permeable container as claimed in claim 2, wherein the open bottom end of the of the container has a width that is more narrow than a width of the lid.

15. The permeable container as claimed in claim 1, wherein the top wall is permeable.

16. The permeable container as claimed in claim 1, wherein the sharp-edged opening on bottom end of the container is provided for pushing into a sample that is to be fixed and/or stabilized, and wherein a portion of the sample that is brought into the permeable container can be separated from the rest of the sample by a rotary movement.

17. The permeable container as claimed in claim 1, wherein the overall height of the container is not more than 5 mm.

18. The permeable container as claimed in claim 1, wherein the distance between the front wall and the back wall is not more than 10 mm.

* * * * *